US010547917B2

(12) United States Patent
Copeland et al.

(10) Patent No.: US 10,547,917 B2
(45) Date of Patent: Jan. 28, 2020

(54) RIDE QUALITY MOBILE TERMINAL DEVICE APPLICATION

(71) Applicant: OTIS ELEVATOR COMPANY, Farmington, CT (US)

(72) Inventors: George Scott Copeland, Wethersfield, CT (US); Jinho Song, Farmington, CT (US)

(73) Assignee: OTIS ELEVATOR COMPANY, Farmington, CT (US)

( * ) Notice: Subject to any disclaimer, the term of this patent is extended or adjusted under 35 U.S.C. 154(b) by 25 days.

(21) Appl. No.: 15/593,707

(22) Filed: May 12, 2017

(65) Prior Publication Data

US 2018/0332368 A1    Nov. 15, 2018

(51) Int. Cl.
| | |
|---|---|
| *B66B 27/00* | (2006.01) |
| *H04Q 9/00* | (2006.01) |
| *G01N 29/14* | (2006.01) |
| *B66B 5/00* | (2006.01) |
| *H04W 4/33* | (2018.01) |
| *H04W 4/38* | (2018.01) |

(Continued)

(52) U.S. Cl.
CPC .............. *H04Q 9/00* (2013.01); *B66B 5/0025* (2013.01); *B66B 5/0087* (2013.01); *B66B 27/00* (2013.01); *G01N 29/14* (2013.01); *H04L 41/22* (2013.01); *H04L 67/1097* (2013.01); *H04L 67/12* (2013.01); *H04W 4/33* (2018.02); *H04W 4/38* (2018.02); *G06F 3/0482* (2013.01); *G06F 3/0484* (2013.01); *H04B 1/3827* (2013.01); *H04Q 2209/40* (2013.01)

(58) Field of Classification Search
None
See application file for complete search history.

(56) References Cited

U.S. PATENT DOCUMENTS

| | | | |
|---|---|---|---|
| 4,350,225 A | 9/1982 | Sakata | |
| 4,512,442 A | 4/1985 | Moore | |

(Continued)

FOREIGN PATENT DOCUMENTS

| | | |
|---|---|---|
| CN | 204689297 U | 10/2015 |
| CN | 105035899 A | 11/2015 |

(Continued)

OTHER PUBLICATIONS

"Elevator Speed", https://play.google.com/store/apps/details?id=com.phonegap.elevatorspeed&hl=en.

(Continued)

*Primary Examiner* — Curtis A Kuntz
*Assistant Examiner* — Jerold B Murphy
(74) *Attorney, Agent, or Firm* — Cantor Colburn LLP

(57) ABSTRACT

A passenger conveyor diagnostic system includes a mobile terminal in signal communication with a cloud computing network. The cloud computing network stores at least one diagnostic algorithm. The mobile terminal device is configured to determine ride quality data of a passenger conveyor system, and to exchange the ride quality data with the cloud computing network. The mobile terminal device further displays one or more diagnostic results which are received from the cloud computing network. The diagnostic result is generated by the cloud computing network in response to applying the at least one diagnostic algorithm to the ride quality data.

19 Claims, 6 Drawing Sheets

(51) Int. Cl.
*H04L 12/24* (2006.01)
*H04L 29/08* (2006.01)
G06F 3/0482 (2013.01)
G06F 3/0484 (2013.01)
H04B 1/3827 (2015.01)

(56) References Cited

U.S. PATENT DOCUMENTS

| | | |
|---|---|---|
| 4,697,243 A | 9/1987 | Moore |
| 4,698,780 A | 10/1987 | Mandel |
| 4,750,591 A | 6/1988 | Coste |
| 4,930,604 A | 6/1990 | Schienda |
| 4,936,419 A | 6/1990 | Stadler |
| 4,989,695 A | 2/1991 | Kubo |
| 5,042,621 A | 8/1991 | Ovaska |
| 5,135,079 A | 8/1992 | Shimazaki |
| 5,254,813 A | 10/1993 | Hirashiki |
| 5,522,480 A | 6/1996 | Hofmann |
| 5,616,895 A | 4/1997 | Spiess |
| 5,787,020 A | 7/1998 | Molliere |
| 5,889,239 A | 3/1999 | Blackaby |
| 6,216,539 B1 * | 4/2001 | Johnson ............... G01N 29/14 73/40.5 A |
| 6,604,611 B2 | 8/2003 | Liu |
| 6,763,917 B2 | 7/2004 | Utsunomiya |
| 7,004,289 B2 | 2/2006 | Shrum, III |
| 7,040,458 B2 | 5/2006 | Forsythe |
| 7,073,633 B2 | 7/2006 | Weinberger |
| 7,298,256 B2 | 11/2007 | Sato |
| 7,437,150 B1 | 10/2008 | Morelli |
| 7,484,598 B2 | 2/2009 | Tyni |
| 7,535,355 B2 | 5/2009 | Barone |
| 7,823,706 B2 | 11/2010 | Tyni |
| 8,028,807 B2 | 10/2011 | Deplazes |
| 8,418,815 B2 | 4/2013 | Encinas Carreno |
| 8,540,057 B2 | 9/2013 | Schuster |
| 8,893,858 B2 | 11/2014 | Shi |
| 9,201,841 B2 | 12/2015 | Rubin |
| 9,213,473 B2 | 12/2015 | Hovi |
| 9,309,089 B2 | 4/2016 | Annen |
| 9,394,138 B2 | 7/2016 | Blanc |
| 9,556,002 B2 | 1/2017 | Wilke |
| 2003/0192745 A1 | 10/2003 | Utsunomiya |
| 2004/0262093 A1 | 12/2004 | Forsythe |
| 2007/0290842 A1 | 12/2007 | Barone |
| 2008/0230326 A1 | 9/2008 | Tyni |
| 2010/0094633 A1 | 4/2010 | Kawamura |
| 2011/0240414 A1 | 10/2011 | Encinas Carreno |
| 2013/0246928 A1 | 9/2013 | Hovi |
| 2014/0262629 A1 | 9/2014 | Toutaoui |
| 2015/0284214 A1 * | 10/2015 | Park ..................... B66B 5/0018 187/393 |
| 2016/0104126 A1 * | 4/2016 | Eleid ..................... G06Q 10/20 705/305 |
| 2016/0130114 A1 | 5/2016 | Wilke |

FOREIGN PATENT DOCUMENTS

| | | |
|---|---|---|
| CN | 105293238 A | 2/2016 |
| CN | 104229577 B | 12/2016 |
| JP | 2003192248 A | 7/2003 |
| JP | 2008024420 A | 2/2008 |
| KR | 20130009308 A | 1/2013 |
| WO | 2005118450 A1 | 12/2005 |
| WO | 2006019167 A1 | 2/2006 |
| WO | 2007093665 A1 | 8/2007 |
| WO | 2009126140 A1 | 10/2009 |
| WO | 2014124890 A1 | 8/2014 |
| WO | WO2014200457 | * 12/2014 |
| WO | WO2014200646 | * 12/2014 |
| WO | 2016137960 A1 | 9/2016 |
| WO | 2016193079 A1 | 12/2016 |

OTHER PUBLICATIONS

International Preliminary Report on Patentability for International Application No. PCT/US2008/059605, dated Oct. 21, 2010.
International Search Report and Written Opinion of the International Searching Authority for International Application No. PCT/US2008/059605, dated Dec. 16, 2008.
Kleemann Newsletter, "Kleemann Presents the Lift Tester at "ELEVCON 2012"",http://www.kleemannlifts.com/index.php?option=com_k2&view=item&id=1324:KLEEMANN-PRESENTS-THE-LIFT-TESTER-AT-%E2%80%9CELEVCON-2012%E2%80%9D&lang=en, Feb. 29, 2012, 1 page.
Martin Monteiro, et al., "Using smartphone pressure sensors to measure vertical velocities of elevators, stairways, and drones", arXiv:1607.00363v4 [physics.ed-ph], Oct. 5, 2016, 13 pages.
Written Opinion for PCT Application No. PCT/US2013/044959, dated Mar. 14, 2014, pp. 1-5.
Extended European Search Report for Application No. 18172185.3; Date of Filing May 14, 2018; dated Mar. 27, 2019 (10 pages).

* cited by examiner

RIDE QUALITY MOBILE TERMINAL DEVICE APPLICATION

BACKGROUND

The present disclosure relates generally to passenger conveyor systems, and more particularly, to passenger conveyor maintenance and operational diagnostics.

Service providers of passenger conveyor systems such as elevator systems, escalator systems, etc., for example, typically rely on user complaints to alert of an existing malfunction or fault before the necessary components are repaired or replaced. Not only must the system to be taken off-line at unscheduled times because it is not known when a component or system will malfunction, but one or more follow-up visits are often required once the problem is identified in order to acquire ride quality data for accurate diagnosis. In addition, diagnosis and monitoring of passenger conveyor systems before and after component faults are identified requires access to circuitry, control boxes, drive systems, or components that may be hidden behind various panels or otherwise out of sight during normal operation. Accessing the circuitry, control boxes, drive systems, or other components may also require that the system be taken out-of-service to provide a technician access to the necessary components.

SUMMARY

A passenger conveyor diagnostic system includes a mobile terminal in signal communication with a cloud computing network. The cloud computing network stores at least one diagnostic algorithm. The mobile terminal device is configured to determine ride quality data of a passenger conveyor system, and to exchange the ride quality data with the cloud computing network. The mobile terminal device further displays one or more diagnostic results which are received from the cloud computing network. The diagnostic result is generated by the cloud computing network in response to applying the at least one diagnostic algorithm to the ride quality data.

Another non-limiting embodiment provides a method of diagnosing a passenger conveyor system. The method includes storing at least one diagnostic algorithm in a cloud computing network, and determining, via a mobile terminal device in signal communication with the cloud computing network, ride quality data of the passenger conveyor system. The method further includes exchanging the ride quality data with the cloud computing network, and displaying at least one diagnostic result in response receiving a diagnostic result received from the cloud computing network. The diagnostic result is generated in response to applying the at least one diagnostic algorithm to the ride quality data.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

The term "about" is intended to include the degree of error associated with measurement of the particular quantity based upon the equipment available at the time of filing the application. For example, "about" can include a range of ±8% or 5%, or 2% of a given value.

Figure 1:
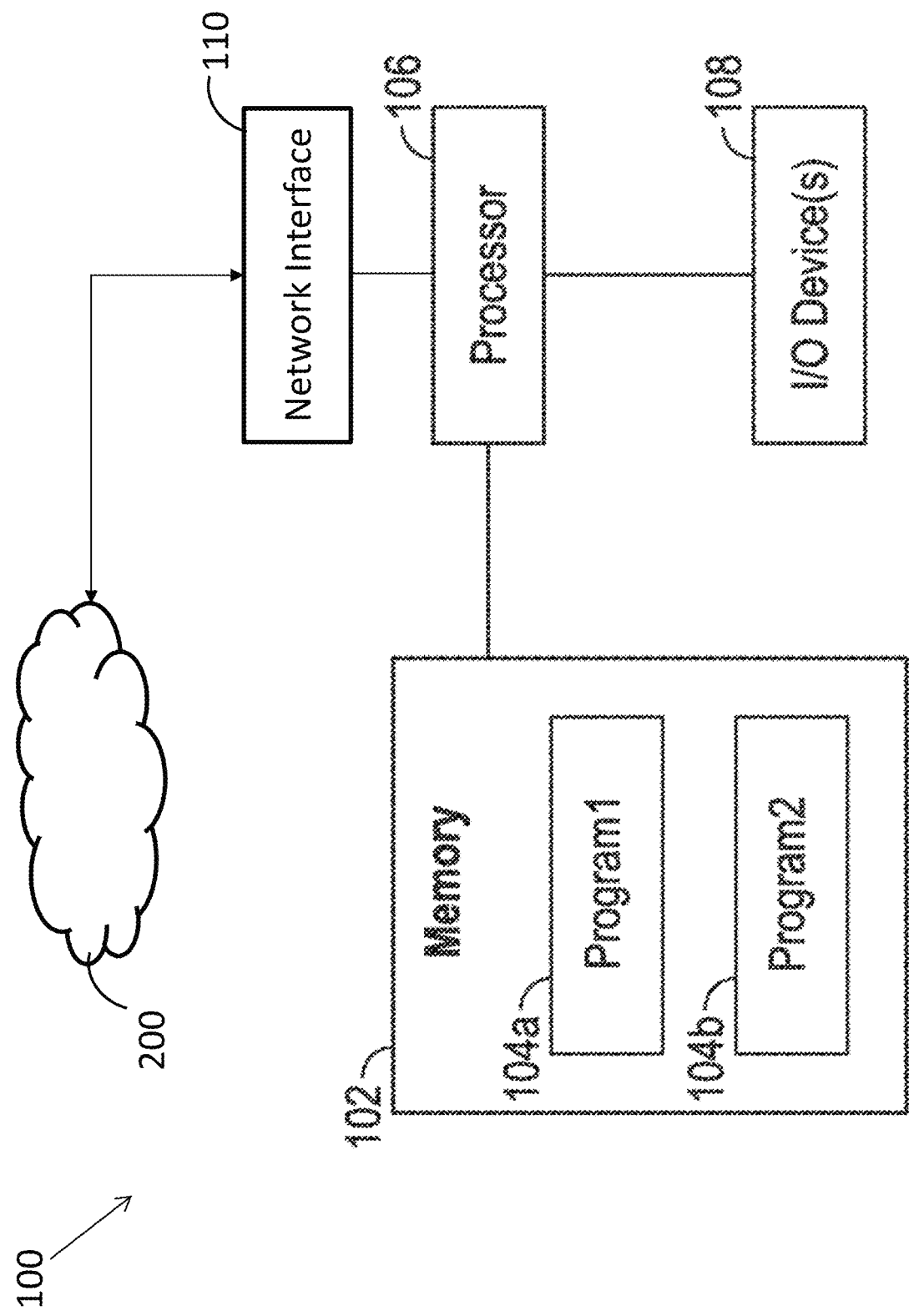
FIG. 1 is a block diagram of a computing system according to a non-limiting embodiment.

With reference now to FIG. 1, a computing system 100 capable of performing one or more embodiments of the invention is illustrated. The computing system 100 includes a memory 102 and an electronic hardware processor 106. The memory 102 stores various instructions algorithms which are executable by the processor 106. The executable instructions can be stored or organized in any manner and at any level of abstraction, such as in connection with one or more processes, routines, procedures, methods, functions, etc. As an example, at least a portion of the instructions are shown in FIG. 1 as being associated with a first program 104a and a second program 104b.

The processor 106 can electrically communicate with the memory 102 via one or more input/output (I/O) devices 108. In some embodiments, the I/O device(s) 108 may include one or more of a keyboard or keypad, a touchscreen or touch panel, a display screen, a microphone, a speaker, a mouse, a button, a remote control, a joystick, a printer, a telephone or mobile device (e.g., a smartphone), etc. The I/O device(s) 108 may be configured to provide an interface to allow a user to interact with the system 100.

The computing system 100 further includes a network interface 110 capable of electrically communication with a cloud computing network 200. The network interface 110 includes any communication device (e.g., a modem, wireless network adapter, etc.) that operates according to a network protocol (e.g., Wi-Fi, Ethernet, satellite, cable communications, etc.) which establishes a wired and/or wireless communication with the cloud computing network 200.

The computing system 100 is illustrative as an example. In some embodiments, one or more of the entities may be optional. In some embodiments, additional entities not shown may be included. For example, in some embodiments the computing system 100 may be associated with one or more networks, such as one or more computer or telephone networks. In some embodiments, the entities may be arranged or organized in a manner different from what is shown in FIG. 1.

Figure 2:
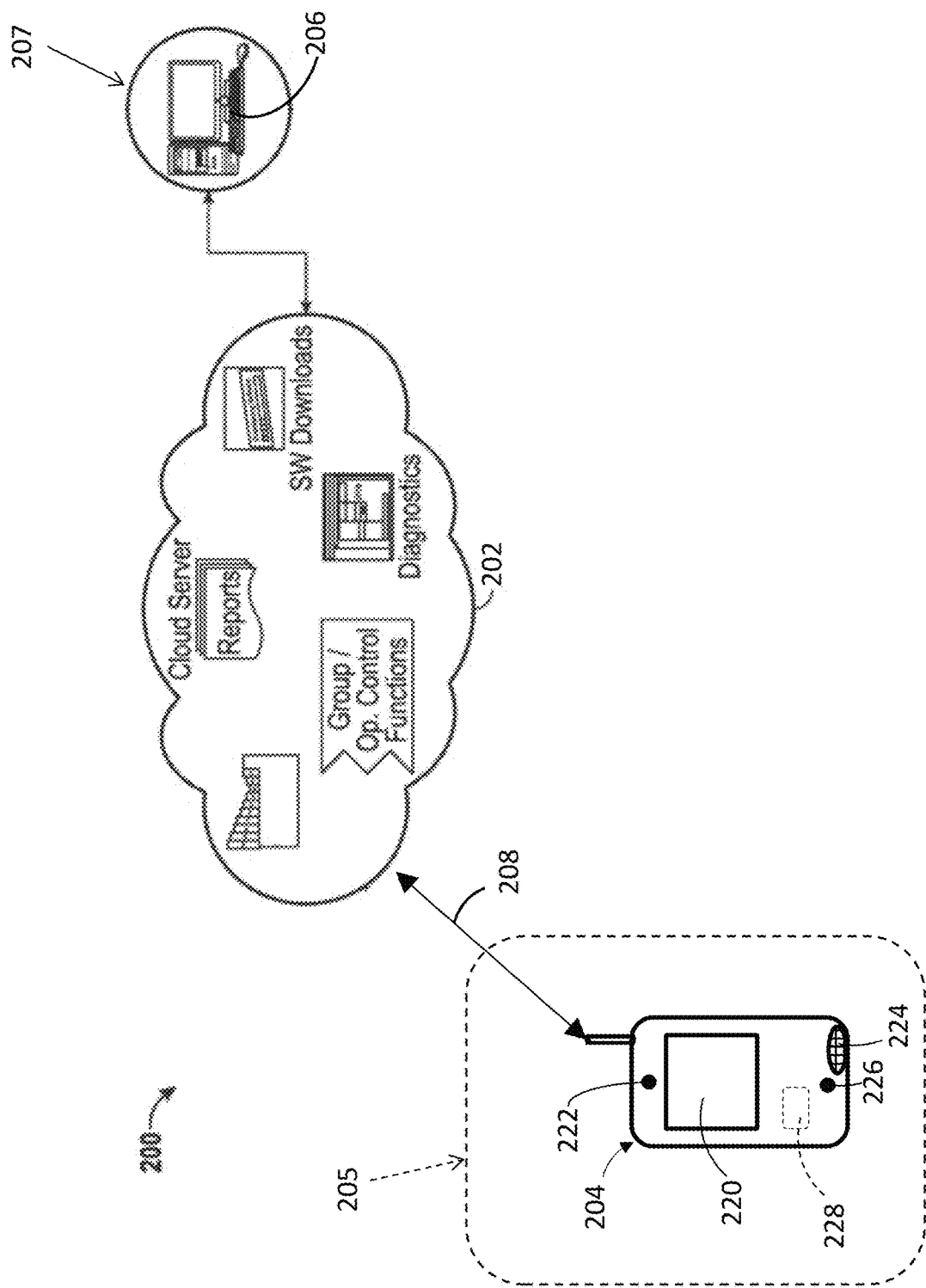
FIG. 2 illustrates a cloud computing network according to a non-limiting embodiment.

Turning now to FIG. 2, a cloud computing network 200 capable of performing one or more embodiments of the invention is illustrated according to a non-limiting embodiment. The cloud computing network 200 includes a cloud server 202, one or more mobile terminal devices 204, and one or more backend computers 206.

The cloud server 202 can store setup parameters for select functions. In some embodiments, the setup parameters can be stored in a controller. In some embodiments, there may be a simplified failover functionality located in the controller in the event that there is a connection loss between the controller and the cloud server 202.

In some embodiments, operational metrics may be collected at a cloud server 202 across a portfolio of multiple units, sites, or groups. The metrics may be analyzed by, e.g., the backend computer 206, to provide a broad view of the portfolio. For example, the analysis may indicate trends and may be used to respond to needs (e.g., product needs or functionality needs). The analysis may also be used to facilitate diagnostic or troubleshooting capabilities. Metrics may be used to trigger or enhance the accuracy of sales proposals. Metrics may be used to provide or schedule maintenance activities, such as preventative maintenance activities. In some embodiments, interface protocols configured to operate with new devices, for example, may be stored in a cloud server 202 and used by a local controller.

In some embodiments, functional upgrades for diagnostics, prognostics, and remote repair/rescue functions can be deployed to customers as they are released and deployed into a cloud server 202. Functionality may be developed at the backend computer 206 (installed at a server location 207 remotely located from the mobile terminal device 204) and deployed to the cloud server 202. One or more tests may be executed to ensure that the functionality satisfies operational or safety requirements.

In some embodiments, a modernization of cloud supported controllers (not shown) may be provided. The controllers can utilize a cloud server 202 to enable new features or support new devices/equipment. Before or during the modernization, the controllers may receive updates via the cloud server 202 to support interface protocols to new equipment and/or add new functions/capabilities. For example, if a new fixture is added requiring a new interface, a controller may enable the new functionality from the cloud server 202 once the new fixture has been integrated into the cloud network 200 without requiring an upgrade of software on the controller. As yet another example, a new dispatching algorithm may be implemented from the cloud to optimize traffic during the modernization phase of the project.

The mobile terminal device 204 is capable of communicating with the cloud server 202 over one or more connections, channels, or links facilitated by a network interface. The mobile terminal device 204 includes a smartphone 204, for example, which can be located in or near a passenger conveyor location 205, and is capable of electrically communicating with the cloud server 202 via a connection 208. The connection 208 can adhere to one or more communication protocols, standards, or the like. For example, the connection 208 can adhere to telephone, cellular, Wi-Fi, Ethernet, satellite, or cable communications. In some embodiments, the connection 208 may be constant or persistent. Although the mobile terminal device 204 will be referred to as a smartphone 204 hereinafter, the mobile terminal device 204 can include any mobile device capable of facilitating interaction between one or more stored software applications (i.e., apps) and the cloud server 202. For example, the mobile terminal device 204 can also include a computer tablet, a laptop computer, a smart watch, etc.

The smartphone 204 includes a display 220, and one or more sensors. The sensors include, but are not limited to, one or more cameras 222, a speaker 224, a microphone 226, and an accelerometer 228. The camera 222 is capable of capturing still images and/or moving images, which the smartphone 204 can reproduce on the display 220. The speaker 224 outputs sound from the smartphone 204 to an external environment. The microphone 226 captures sounds and noise present in the vicinity of the smartphone 204. The captured noise can be recorded to memory and reproduced via the speaker 224. The accelerometer 228 may be constructed as a single-axis or and multi-axis accelerometer, and is capable of detecting magnitude and direction of smartphone's proper acceleration, as a vector quantity. The accelerometer 228 can sense the orientation of the smartphone 204, coordinate acceleration, vibrations, shock, and movements.

As described above, functionality may be (re)located to a cloud server (e.g., cloud server 202). In terms of elevator systems, for example, such functionality may include dispatch functions for one or more passenger conveyor devices, mobile terminals, operational mode determinations, diagnostic functions, special contract features, etc. Regarding dispatch functions, in some embodiments a user request for service received at, e.g., a hall box located on a particular floor of a building may be communicated to the cloud server and the cloud server may transmit a command that directs a specified elevator car to relocate to that particular floor to fulfill the service request.

In some embodiments, a local controller (not shown) can maintain some functionality, and as such, may include hardware and computing resources to support such functionality. The controller can include hardware and/or software to communicate with the cloud server 202. For example, the controller can exchange data and commands with the cloud server 202 to perform control functions.

Figure 3:
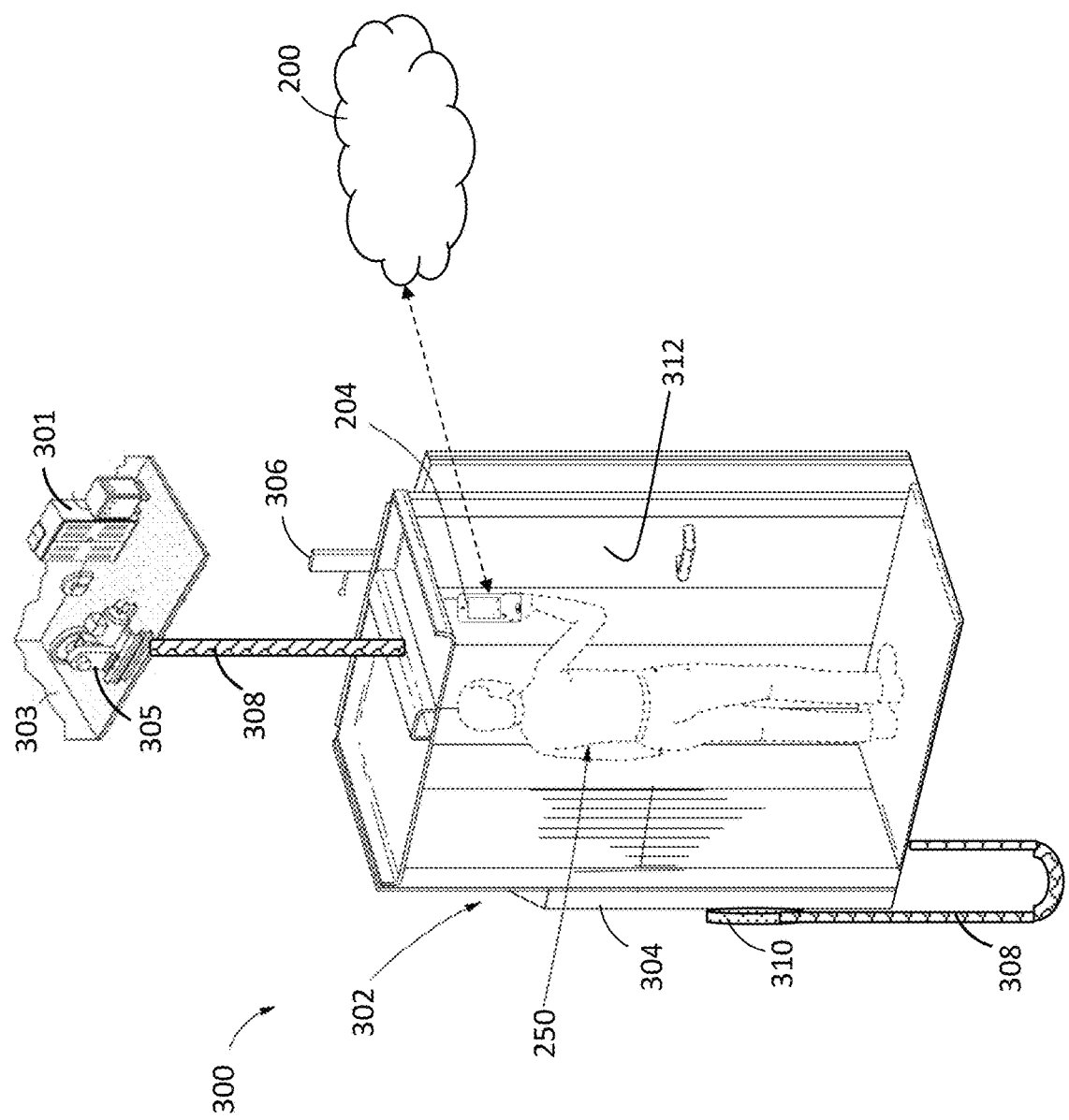
FIG. 3 illustrates a mobile terminal device installed with a ride quality software application operating in the vicinity of an elevator system according to a non-limiting embodiment.

Turning now to FIG. 3, a mobile terminal device 204 installed with a ride quality software application operating in the vicinity of an elevator system 300 is illustrated according to a non-limiting embodiment. Although an elevator system 300 is described with reference to FIG. 3, it should be appreciated that the smartphone 204 can operate in conjunction with other types of passenger conveyor systems including, but not limited to, a vertical escalator system, a horizontal escalator system (i.e., an automated moving walkway system), etc., without departing from the scope of the invention.

The elevator system 300 includes a machine 301 that drives an elevator car 302 positioned in a vertical hoistway (not shown). One or more elevator car rails 304 and guides 306 are attached to the hoistway walls. The elevator system 300 further includes one or more elongated members 308 which couple the elevator car 302 to a counterweight (not shown). In at least one embodiment, the elongated members are formed as round steel ropes 308 configured to support the weight of the elevator car 302 and the counterweight so as to propel the elevator car 302 in a desired direction (e.g., up or down) within the hoistway. Although a single rope 308 is shown, it should be appreciated that additional ropes may be implemented.

The elevator machine 301 is installed in a machine room 303 located remotely from the elevator car 302. The elevator machine 301 controls a traction sheave 305 that rotates and causes movement of the ropes 308 to drive the elevator car 302 in a selected direction. The elevator system 300 further includes one or more deflector or idler sheaves 310 to assist in guiding the movement of various traction ropes 308. In this manner, the elevator car 302 can be driven to one or more landings or floors vertically arranged with respect to one another. Accordingly, the elevator car 302 can be driven to a requested floor, where passengers can then enter or exit the car 302 via the elevator doors 312.

Still referring to FIG. 3, a maintenance technician or mechanic 250 can operate the elevator car 302 while diagnosing the elevator system 300 using a mobile terminal device 204. Although the mobile terminal device 204 will be described as a smartphone, other types of mobile terminal or user equipment (UE) devices may be employed including, but not limited to, a computer tablet, a laptop computer, a smart watch, etc.

The maintenance technician 250 can operate the smartphone 204 to obtain real-time ride quality data of the elevator system 300. For instance, the smartphone 204 can be located near the doors 312 to capture noises (e.g., squeaking) via the microphone and/or images of the door operation via the camera. In another example, the smartphone 204 can detect vibrations, via the accelerometer, as the car 302 travels between one or more floors during an elevator run.

The smartphone 204 is installed with a ride quality software application, and is configured to electrically communicate with a cloud computing network 200 via a network interface device. As described herein, the network interface device includes any communication device (e.g., a modem, wireless network adapter, etc.) that operates according to a network protocol (e.g., Wi-Fi, Ethernet, satellite, cable communications, etc.) which establishes a wired and/or wireless communication with the cloud computing network 200.

The ride quality software application is capable of providing quantitative measurement and analysis of ride quality. For example, the ride quality software application can compare real-time performance of the elevator system 300 to an expected performance. Analytical data generated by the ride quality software application can be stored locally on the smartphone 204 and/or can be stored in the cloud server 202. The analytical data includes, but is not limited to, machine noise, machine vibration, elevator car vibrations, rope noises, transient/travel noise, idler/deflector noises, rail and guide vibrations, and elevator door noise. The analytical data stored in the cloud server 202 and can further be archived and tracked over time to determine whether an identified problem has been resolved following a recent repair effort, or whether the problem remains or has worsened.

Figure 4:
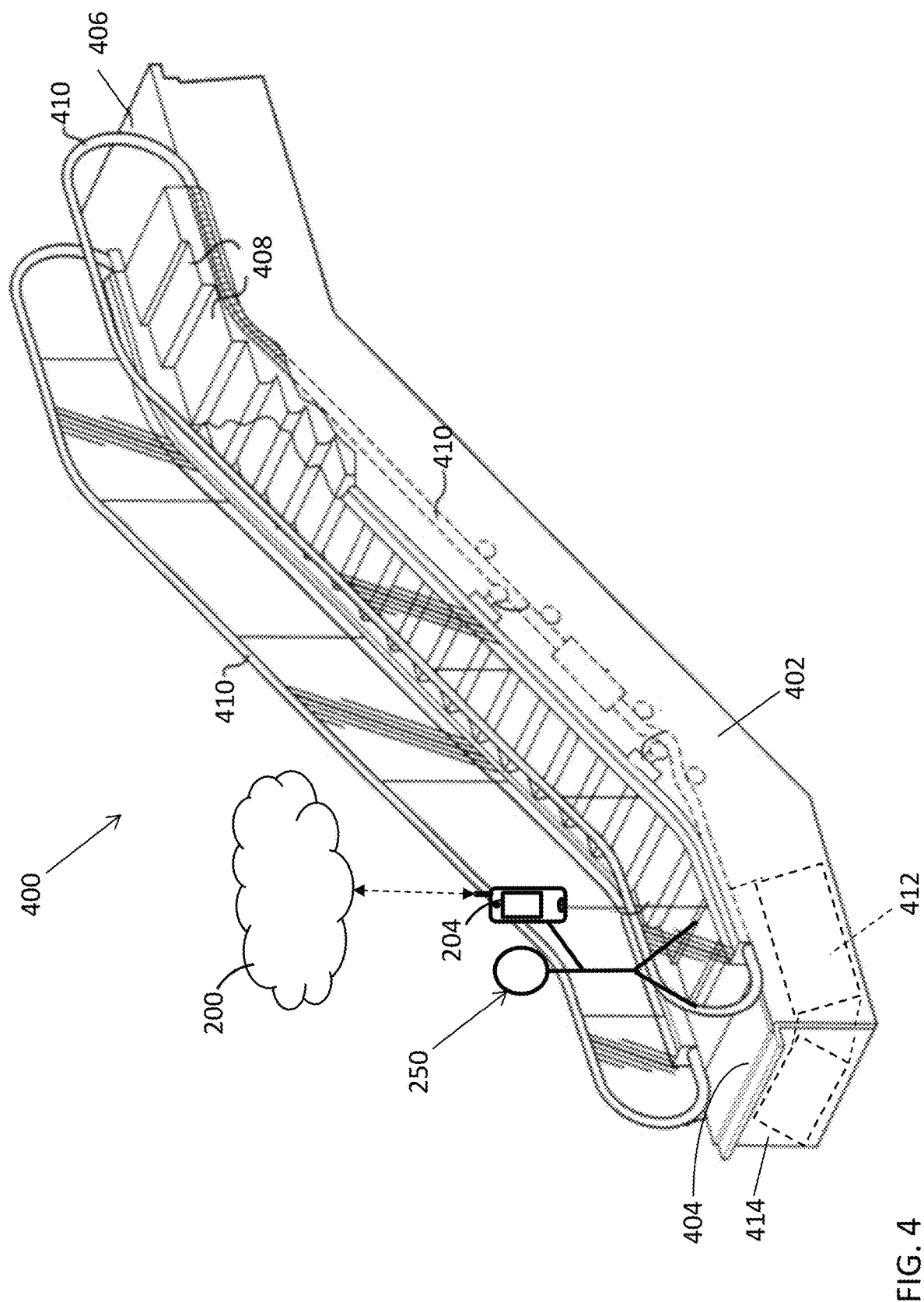
FIG. 4 illustrates a mobile terminal device installed with a ride quality software application operating in the vicinity of an escalator system according to a non-limiting embodiment.

Turning to FIG. 4, a smartphone 204 installed with a ride quality software application operating in the vicinity of an escalator system 400 is illustrated according to a non-limiting embodiment. The escalator system 400 includes a truss 402 extending between a lower landing 404 and an upper landing 406. A plurality of sequentially connected treadplates or steps 408 are connected to a drive chain (not shown) and travel through a closed loop path within the truss 402. A pair of handrails 410 are coupled to the truss 402 and are located at opposing sides of the steps 408. The handrails 410 move along with the steps 408 to provide passenger support. A machine 412 drives the steps 408 and handrails 410. The machine 412 is typically located in a machine space 414 under one of the landings e.g., contained within the lower landing 404.

Still referring to FIG. 4, a maintenance technician or mechanic 250 can diagnose operation of the escalator system 400 using a mobile terminal device 204 such as, for example a smartphone 204, which is installed with a ride quality software application. As described above, other types of mobile terminal UE devices may be employed including, but not limited to, a computer tablet, a laptop computer, smart watch, etc.

A maintenance technician or mechanic 250 can operate the smartphone 204 to obtain real-time ride quality data of the escalator system 400. For instance, the smartphone 204 can be located near the handrails 410 to capture noises (e.g., squeaking) via the microphone, and/or can be placed against the handrails 410 to detect vibrations via the accelerometer. In another example, the smartphone 204 can be located in or near the machine space 414 to record the sounds of the machine 412. In still another example, the camera of the smartphone can capture images of the moving steps 408 and/or handrails 410.

The smartphone 204 is configured to electrically communicate with a cloud computing network 200 via a network interface device. As described herein, the network interface device includes any communication device (e.g., a modem, wireless network adapter, etc.) that operates according to a network protocol (e.g., Wi-Fi, Ethernet, satellite, cable communications, etc.) which establishes a wired and/or wireless communication with the cloud computing network 200.

The ride quality software application is capable of providing quantitative measurement and analysis of the ride quality obtained by the smartphone 204. For example, the ride quality software application is capable of performing real-time comparisons between actual performance of the escalator system 400 and its expected performance. Analytical data generated by the ride quality software application can be stored locally on the smartphone 204 and/or can be stored in the cloud server 202. The analytical data includes, but is not limited to, machine noise, machine vibration, truss vibrations, step vibrations, step noise, handrail vibrations, handrail noise, and drive chain noise. The analytical data stored in the cloud server 202 can further be archived and tracked over time determine whether an identified problem has been resolved following a recent repair effort, or whether the problem remains or has worsened.

Figure 5:
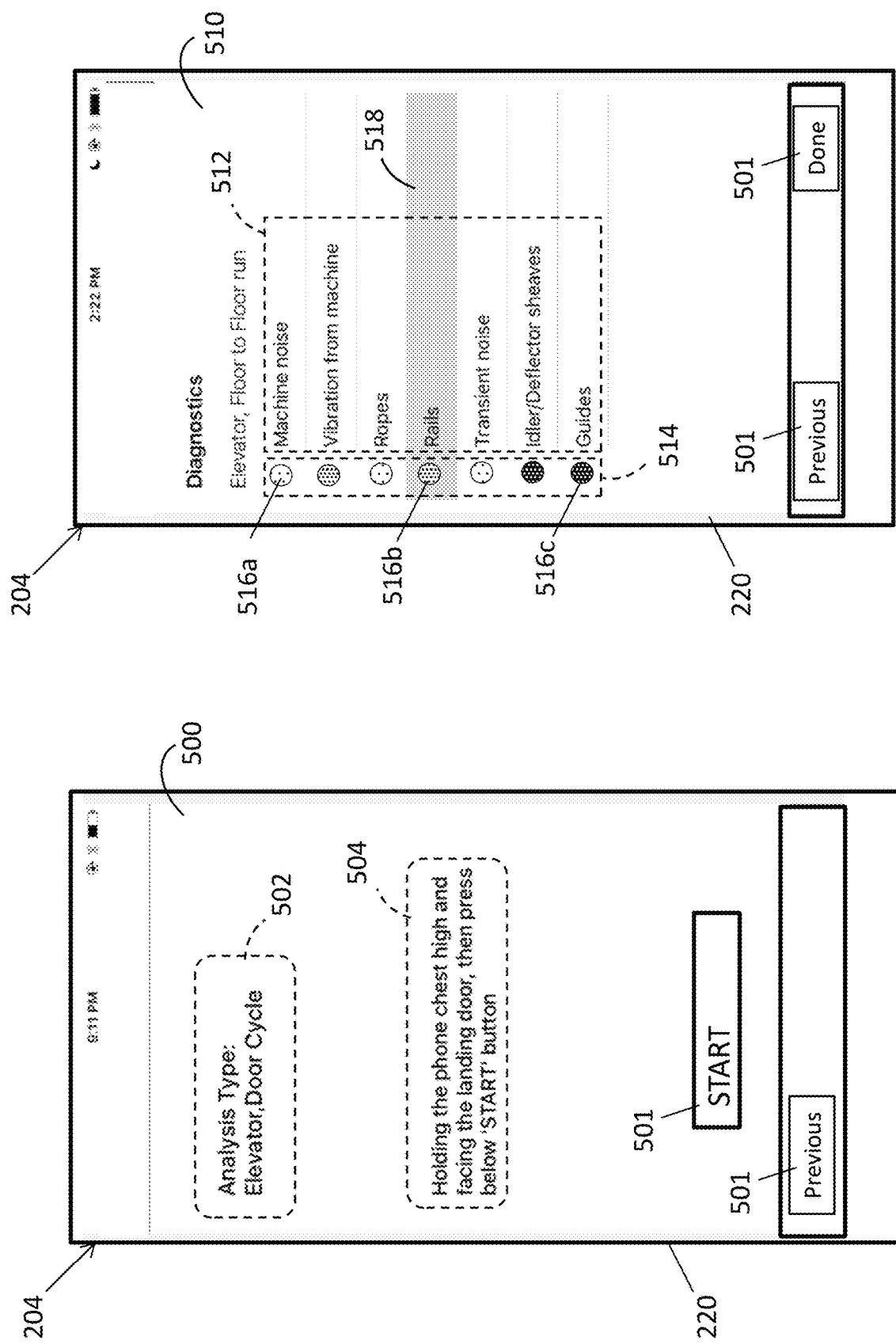
FIG. 5A illustrates a mobile terminal device displaying a home interface provided by a ride quality software application according to a non-limiting embodiment.
FIG. 5B illustrates a mobile terminal device displaying a diagnostic results interface provided by a ride quality software application according to a non-limiting embodiment.

Referring to FIGS. 5A and 5B, a smartphone 204 is illustrated operating in various modes. Each modes displays a corresponding graphic user interfaces (GUI) according to a non-limiting embodiment. Referring to FIG. 5A, the smartphone 204 is shown operating in a diagnostic selection mode which presents a smartphone user (e.g., maintenance technician) with a home GUI 500. A user can manipulate the home GUI 500 by touching a touch-screen actuator 501 displayed on the screen 220 and/or using other input actuators (not shown) installed on the smartphone 204.

The home GUI 500 includes a diagnostic selection field 502 and a user instruction field 504. The diagnostic selection field 502 allows the user to select a desired diagnostic operation among a plurality of different diagnostic operations capable of diagnosing different maintenance issues of a passenger conveyor system. In terms of an elevator system environment, for example, the various diagnostic operations include, but are not limited to, a "Door Cycle" diagnostic operation and a "Floor-to-Floor" diagnostic operation. The "Door Cycle" diagnostic test executes a testing routine to diagnose the operation of the elevator doors. The "Floor-to-Floor" diagnostic operation executes a testing routine to diagnose any abnormal or sub-optimal operation of the elevator as it travels within the building.

In terms of an escalator system environment, the diagnostic selection field 502 allows a user to select from various diagnostic operations including, but are not limited to, a Machine Diagnostic, an Ascending Step Run diagnostic, a Descending Step Run diagnostic a Handrail Diagnostic, and a Braking Diagnostic. As in the case of elevator diagnostic tests described above, the abnormal or sub-optimal noise and vibrations can be analyzed to implicate a particular product part or component. Symptoms and diagnoses can be displayed on the screen.

The Machine Diagnostic operation allows for capturing noises generated from within the machine space and compares the measured noises to the expected range of noises for that equipment.

The Ascending Step Run and Descending Step Run Diagnostic operations monitor real-time operation of the escalator system as the user rides along with the moving steps. The diagnostics during this operation include, sound detection of step and handrail noises, noises of the drive chain, vibrations of the steps, and step traveling speed.

The Handrail Diagnostic can be more specifically directed to diagnosing issues with the handrail. The diagnostics performed during the Handrail Diagnostic includes analyzing noises produced by the handrails and/or vibrations of the handrails.

The Braking Diagnostic can diagnose whether the steps of the escalator are brought to a stop in an expected amount of time following an escalator braking event. The deceleration of the steps can be compared to a threshold to determine whether the braking function of the escalator is performing as expected. The Braking Diagnostic can also diagnostic the deceleration of the steps. For example, any pulsations in the deceleration of the steps can implicate specific parts or components of the braking mechanism.

The user instruction field 504 displays diagnostic operating instructions that direct the user how to properly execute the selected diagnostic operation. The instructions include, for example, instructing a user where to locate the smartphone with respect to the user's person, along with a location with respect to the passenger conveyor system while will provide the user with most optimal results. When the "Door Cycle" diagnostic is selected, for example, the user instruction field 504 can instruct the user to "hold the phone chest high, face the landing door, and press start." The instructions presented in the user instruction field 504 can vary based on the diagnostic operation selected from the diagnostic selection field 502. For example, when performing the Door Cycle diagnostic, the instructions may instruct the user to locate the smartphone 204 near the elevator doors or near a specific component associated with the doors, whereas instructions corresponding to the Machine Diagnostic instructions will instruct the user to locate the phone within the machine space of the escalator. Similar instructions can be provided to the user when performing diagnostic operations associated with another type of passenger conveyor system such as, for example, an escalator system.

Turning to FIG. 5B, the smartphone 204 is shown operating in a diagnostic results mode which presents a smartphone user with a diagnostics results GUI 510 following completion of a corresponding diagnostic operation. The diagnostic results GUI 510 includes a component field 512 and a status indicator field 514. The component field 512 lists one or more components that were diagnosed according to a selected diagnostic operation (i.e., the diagnostic operation selected from the home GUI 500). One or more of the displayed components can change depending on the selected diagnostic operation. For example, "ropes" and "rails" may be displayed after performing the Floor-to-Floor diagnostic operation, while "sill" and "hanger" may be displayed after performing the Door Cycle diagnostic operation. Similarly, escalator components such as "step chain" and "handrail drive chain", for example, may be displayed after performing one or more escalator system diagnostic operations.

The status indicator field 514 displays a status indicator 516a, 516b, and 516c corresponding to each component name displayed in the component field 512. The status indicator 516a-516c can be displayed with a unique identified (e.g., color, shape, etc.) which indicates a diagnosed status of the component following the diagnostic operation. For example, a first status indictor 516a (e.g., a green-colored graphical indicator) may indicate that the corresponding component is operating normally or as expected following the diagnostic operation. A second status indictor 516b (e.g., a yellow-colored graphical indicator) may indicate that although still providing suitable results, a corresponding component was detected as operating with one or more irregularities. For example, although an elevator car traveled between one or more floors with noise levels that are generally acceptable to most passengers, the noise may contain features that suggest a roller bearing is wearing and should be replaced. Therefore, the maintenance technician may monitor this unit carefully for the next several service visits. A third status indicator 516c (e.g., a red-colored graphical indicator) may indicate that service should be performed in order to assure that the unit consistently meets customer expectations. These results may include, for example, vibrations or noises that exceed a threshold level for passenger comfort. The diagnostic information may implicate particular parts or components so that the service personnel will be properly prepared for a successful service on the first visit.

The diagnostic results GUI 510 further includes a component selector 518, which can be manipulated by a user to highlight and select a given component name displayed on the screen 220. In response to selecting the highlighted component name, additional information concerning the selected component can be provided to the user. This could include for example, the distance travelled at which an unexpected noise occurred, or the characteristic frequency and likely cause of a persistent noise. Noise measurements can be played back through the speaker of the smartphone 204 allowing the user to hear noises that may have been overlooked. In another example, a video of the actual operation of the selected component (e.g., the doors) can be played on the display screen 220 alongside a pre-recorded video showing the expected operation of the doors. In addition, electronic maintenance manuals and/or schematics of the components or relevant component system can be displayed on the screen 220 to further assist the user in diagnosing the selected component. According, a service technician can immediately identify one or more problem components and attempt to resolve the abnormalities without passenger input.

Figure 6:
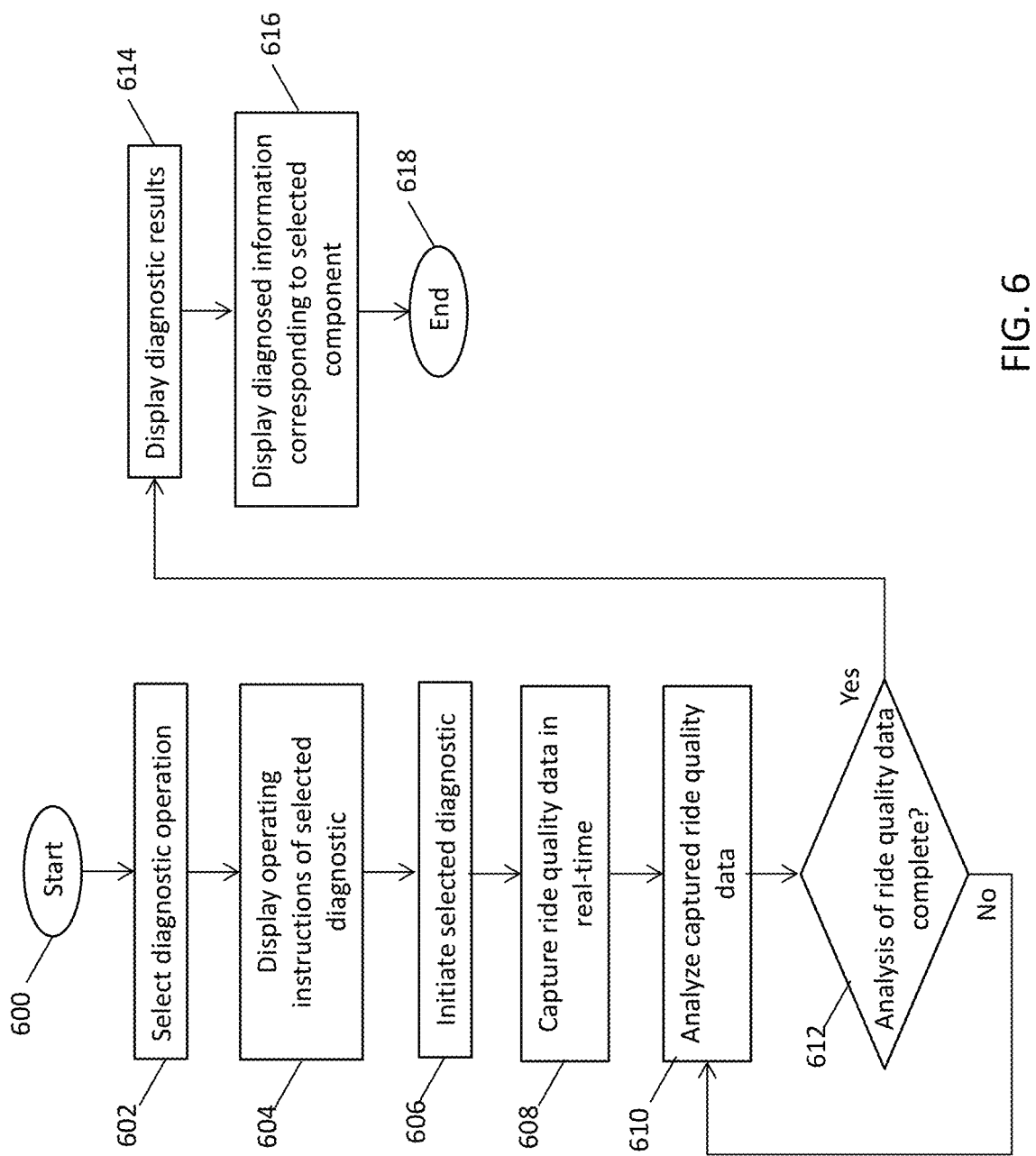
FIG. 6 is a flow diagram illustrating a method of diagnosing a passenger conveyor system using a ride quality software application installed on mobile terminal device according to a non-limiting embodiment.

Turning now to FIG. 6, a flow diagram illustrates a method of diagnosing a passenger conveyor system using a ride quality software application installed on an electronic mobile terminal device according to a non-limiting embodiment. The method begins at operation 600, and at operation 602 a diagnostic is selected among one or more available diagnostic operations. At operation 604, diagnostic operating instructions corresponding to the selected diagnostic are displayed on a screen of the mobile terminal device. At operation 606, the selected diagnostic operation is initiated, and one or more diagnostic algorithms are executed. At operation 608, real time ride quality data of the passenger conveyor system is obtained. The ride quality data includes noises, sounds, vibrations, and images captured during the real-time operation of the passenger conveyor system. At operation 610, the real-time data is analyzed using various algorithms and processing applications. For example, real-time captured sounds can be compared to pre-recorded expected sounds to determine whether an unexpected sound is present, or whether expected sounds exceed a predetermined sound threshold. At operation 612, a determination is made as to whether the diagnostic is complete. When the diagnostic is not complete, the method returns to operation 610 and continues analyzing the real-time data.

When, however, the diagnostic is complete at operation 612, the method proceeds to operation 614 and displays one or more diagnostics results on a screen of the mobile terminal device. In at least one embodiment, the mobile terminal device generates a diagnostic results GUI, which displays a diagnostic status indictor corresponding to each component diagnosed according to the selected diagnostic operation. When a user selects a particular component name from the diagnostic results GUI, the GUI displays additional diagnostic information concerning the selected component at operation 616 (e.g., real-time captured noises, images, electronic schematics, etc.), and the method ends at operation 618.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A passenger conveyor diagnostic system, comprising:
   a cloud computing network that stores at least one diagnostic algorithm; and
   a mobile terminal device in signal communication with the cloud computing network, the mobile terminal device configured to determine ride quality data of a passenger conveyor system, and to exchange the ride quality data with the cloud computing network,
   wherein the mobile terminal device displays at least one diagnostic result in response receiving a diagnostic result received from the cloud computing network, the diagnostic result generated in response to applying the at least one diagnostic algorithm to the ride quality data,
   wherein the mobile terminal device operates in a first mode that generates a first graphical user interface (GUI) relating to a diagnostic operation and displays operating instructions in response to selecting the diagnostic operation, and a second mode that generates a GUI configured to display diagnostic results provided by the least one diagnostic algorithm corresponding to the diagnostic operation from the first GUI,
   wherein different components to be diagnosed are automatically determined according to the selected diagnostic operation, wherein the second mode of the GUI displays the diagnostic results for each component determined in response to performing the selected diagnostic operation.

2. The passenger conveyor diagnostic system of claim 1, wherein the passenger conveyor system is an elevator system.

3. The passenger conveyor diagnostic system of claim 2, wherein the ride quality data includes at least one of machine noise, elevator door noise, elevator car noise, and elevator car vibration.

4. The passenger conveyor diagnostic system of claim 1, wherein the passenger conveyor system is an escalator system.

5. The passenger conveyor diagnostic system of claim 4, wherein the ride quality data includes at least one of machine noise, step vibration, step noise, drive chain noise, handrail noise, handrail vibration, step speed, and braking speed.

6. The passenger conveyor system of claim 1, wherein the mobile terminal device operates in the first mode to select a diagnostic operation among a plurality of available diagnostic operations, and wherein the GUI of the second mode displays the diagnostic results provided by the least one diagnostic algorithm corresponding to the diagnostic operation selected from the first GUI.

7. The passenger conveyor system of claim 1, wherein the mobile terminal device is one of a smartphone, a computer tablet, or a smart watch.

8. A mobile terminal device configured to diagnose a passenger conveyor system, the mobile terminal device comprising:
   a memory unit that stores a ride quality application;
   at least one sensor configured to determine ride quality data of the passenger conveyor system;
   a network interface device that establishes communication with a cloud computing network; and
   an electronic hardware controller that exchanges the ride quality data with the cloud computing network via the network interface device, and that generates at least one graphical user interface (GUI) displayed on a screen of the mobile terminal device, the GUI displaying at least one diagnostic result of the passenger conveyor system,
   wherein the controller invokes a first mode that generates a first graphical user interface (GUI) relating to a diagnostic operation and displays operating instructions in response to selecting the diagnostic operation, and a second mode that generates a GUI configured to display diagnostic results provided by the least one diagnostic algorithm corresponding to the diagnostic operation from the first GUI,
   wherein different components to be diagnosed are automatically determined according to the selected diagnostic operation, wherein the second mode of the GUI displays the diagnostic results for each component determined in response to performing the selected diagnostic operation.

9. The mobile terminal device of claim 8, wherein the ride quality data includes at least one of elevator machine noise, elevator door noise, elevator car noise, elevator car vibration, escalator machine noise, escalator step vibration, escalator step noise, escalator step speed, escalator handrail noise, escalator handrail vibration, and escalator braking speed.

10. The mobile terminal device of claim 9, wherein the controller invokes the first mode to select a diagnostic operation among a plurality of available diagnostic operations, and wherein the GUI of the second mode displays the diagnostic results provided by the least one diagnostic algorithm corresponding to the diagnostic operation selected from the first GUI.

11. The mobile terminal device of claim 8, wherein the mobile terminal device is one of a smartphone, a computer tablet, or a smart watch.

12. The mobile terminal device of claim 8, wherein the GUI of the second mode displays at least one diagnostic result corresponding to the components of the passenger conveyance system determined in response to executing the selected diagnostic operation.

13. The mobile terminal device of claim 12, wherein the at least one diagnostic result includes at least one of a recorded noise corresponding to the component, an image of the component, a schematic corresponding to the component, and maintenance instructions corresponding to the component.

14. A method of diagnosing a passenger conveyor system, the method comprising:
storing at least one diagnostic algorithm in a cloud computing network; and
determining, via a mobile terminal device in signal communication with the cloud computing network, ride quality data of the passenger conveyor system;
exchanging the ride quality data with the cloud computing network; and
displaying at least one diagnostic result in response receiving a diagnostic result received from the cloud computing network, the diagnostic result generated in response to applying the at least one diagnostic algorithm to the ride quality data, wherein displaying the at least one diagnostic result further comprises:
operating the mobile terminal in a first mode that generates a first graphical user interface (GUI) related to a diagnostic operation; and
operating the mobile terminal in a second mode that generates a GUI configured to display diagnostic results provided by the least one diagnostic algorithm corresponding to the diagnostic operation from the first GUI,
wherein different components to be diagnosed are automatically determined according to the selected diagnostic operation, wherein the second mode of the GUI displays the diagnostic results for each component determined in response to performing the selected diagnostic operation.

15. The method of claim 14, wherein the ride quality data includes at least one of elevator machine noise, elevator door noise, elevator car noise, elevator car vibration, escalator machine noise, escalator step vibration, escalator step noise, escalator step speed, escalator handrail noise, escalator handrail vibration, and escalator braking speed.

16. The method of claim 15, wherein the mobile terminal device is one of a smartphone, a computer tablet, or a smart watch.

17. The method of claim 15, further comprising operating the mobile terminal in the first mode to select a diagnostic operation among a plurality of available diagnostic operations, and wherein the GUI operating of the second mode displays the diagnostic results provided by the least one diagnostic algorithm corresponding to the diagnostic operation selected from the first GUI.

18. The method of claim 17, wherein the ride quality data includes at least one of elevator machine noise, elevator door noise, elevator car noise, elevator car vibration, escalator machine noise, escalator step vibration, escalator step noise, escalator step speed, escalator handrail noise, escalator handrail vibration, and escalator braking speed.

19. The method of claim 18, wherein the at least one diagnostic result includes at least one of a visual indicator including at least one of a colored graphic, a text message providing explanation of the result, recorded noise corresponding to the component, an image of the component, a schematic corresponding to the component, and maintenance instructions corresponding to the component.

* * * * *